United States Patent
Spindler et al.

(10) Patent No.: US 6,218,559 B1
(45) Date of Patent: Apr. 17, 2001

(54) HYDROGENATION CATALYST, PROCESS FOR THE PREPARATION THEREOF AND HYDROGENATION PROCESS

(75) Inventors: Felix Spindler, Starrkirch-Wil (CH); Ulrich Pittelkow, Rheinfelden (DE)

(73) Assignee: Novaritis Corporation, Greensboro, NC (US)

( * ) Notice: Subject to any disclaimer, the term of this patent is extended or adjusted under 35 U.S.C. 154(b) by 0 days.

(21) Appl. No.: 09/267,486

(22) Filed: Mar. 11, 1999

Related U.S. Application Data

(62) Division of application No. 08/871,478, filed on Jun. 9, 1997, now Pat. No. 5,912,375, which is a continuation of application No. 08/687,333, filed as application No. PCT/EP95/00222 on Jan. 21, 1995, now abandoned.

(30) Foreign Application Priority Data

Feb. 2, 1994 (CH) ....................................... 310/94

(51) Int. Cl.$^7$ ................ C07F 7/26; C07F 17/02
(52) U.S. Cl. ................ 556/14; 556/19; 556/20; 556/21; 556/23
(58) Field of Search .................. 556/14, 19, 20, 556/21, 23

(56) References Cited

U.S. PATENT DOCUMENTS

| | | | |
|---|---|---|---|
| 4,994,615 | 2/1991 | Spindler et al. | 564/304 |
| 5,011,995 | 4/1991 | Pugin et al. | 564/302 |
| 5,112,999 | 5/1992 | Osborn et al. | 556/23 |
| 5,187,281 | 2/1993 | Kolich et al. | 556/16 |
| 5,371,256 | 12/1994 | Togni et al. | 556/14 |

FOREIGN PATENT DOCUMENTS

| | | |
|---|---|---|
| 256982 | 2/1988 | (EP) . |
| 419409 | 3/1991 | (EP) . |
| 564406 | 10/1993 | (EP) . |

OTHER PUBLICATIONS

Journal of Organometallic Chemistry, Bennet et al., vol. 118, 1976 Lausanne, pp. 205–232.

*Primary Examiner*—Mukund J. Shah
*Assistant Examiner*—Tamthom N. Truong
(74) *Attorney, Agent, or Firm*—William A. Teoli, Jr.

(57) ABSTRACT

Reaction products of an iridium(III) salt or a hydrate thereof, a diphosphine having secondary phosphine groups and a metal or ammonium chloride, bromide or iodide are excellent hydrogenation catalysts for ketimine. Using chiral diphosphines and prochiral ketimines, diastereoisomeric secondary amines are obtained in high optical yields.

21 Claims, No Drawings

HYDROGENATION CATALYST, PROCESS FOR THE PREPARATION THEREOF AND HYDROGENATION PROCESS

This application is a division of Ser. No. 871,478, filed Jun. 9, 1997 (now U.S. Pat. No. 5,912,375), which is a continuation of Ser. No. 687,333, filed Aug. 12, 1996 (now abandoned) which is a 371 of PCT EP95/00222, filed Jan. 21, 1995.

The present invention relates to a catalyst obtainable by the reaction of iridium salts with diphosphines and alkali metal or ammonium halides; to a preparation process for those catalysts; and to a process for the hydrogenation of imines, especially in the presence of an acid.

U.S. Pat. No. 4,994,615 describes a process for the asymmetric hydrogenation of prochiral N-arylketimines wherein iridium catalysts having chiral diphosphine ligands are used. U.S. Pat. No. 5,011,995 describes a process for the asymmetric hydrogenation of prochiral N-alkylketimines using the same catalysts. U.S. Pat. No. 5,112,999 discloses polynuclear iridium compounds and a complex salt of iridium, which contain diphosphine ligands, as catalysts for the hydrogenation of imines. The catalysts are prepared by reacting iridium olefin and iridium diolefin complexes with diphosphines.

Those homogeneous catalysis processes have proved valuable, although it is evident, especially in the case of relatively large batches or on an industrial scale, that the catalysts frequently tend to become deactivated to a greater or lesser extent depending on the catalyst precursor, the substrate and the diphosphine ligands that are used In many cases, especially at elevated temperatures—for example at temperatures >25° C., which are necessary for a short reaction time—it is not possible to achieve complete conversion. For industrial applications of the hydrogenation process, therefore, the catalyst productivity is too low from the point of view of economic viability.

A further disadvantage is the fact that as starting materials for the catalysts the iridium olefin and iridium diolefin complexes are unstable and expensive, with the result that it is not possible in practice to obtain commercial quantities.

It has now been found, surprisingly, that active homogeneous iridium catalysts can be obtained from simple iridium salts, which are considerably more economical, by reacting those salts with diphosphines in the presence of metal halides, especially alkali metal or ammonium halides.

It has also been found, surprisingly, that the catalyst activity can be increased if during the hydrogenation the reaction mixture comprises an acid in addition to the catalyst. It has also unexpectedly been found that at the same time the deactivation of the catalysts can be considerably reduced or completely eliminated.

The invention relates to iridium compounds that are obtainable by reacting iridium(III) or iridium(IV) salts or hydrates thereof and a diphosphine having secondary phosphine groups in the presence of a metal chloride, bromide or iodide or an ammonium chloride, bromide or iodide.

The iridium(IU) salts or hydrates thereof may be, for example, of formula I $$[Ir^{3\oplus}][X^{n\ominus}]_{3/n} \cdot mH_2O \tag{I}$$

wherein X is the n-valent anion of an acid, n is 1, 2 or 3, and m is 0 or a whole number or a fraction greater than 0 and up to 8.

The iridium(IV) salts or hydrates thereof may be, for example, of formula Ia $$M_2^{\oplus}[IrX'_6]^{2\ominus} \cdot mH_2O \tag{Ia}$$

wherein

X' is halogen, especially F, Cl or Br, $M_2^{\oplus}$ is two $H^{\oplus}$, two alkali metal cations, for example $Li^{\oplus}$, $Na^{\oplus}$ or $K^{\oplus}$, or an alkaline earth metal cation, for example $Mg^{2\oplus}$, $Ca^{2\oplus}$, $Sr^{2\oplus}$ or $Ba^{2\oplus}$, and m is 0 or a whole number or a fraction greater than 0 and up to 8.

In formulae I and/or Ia, n is preferably 1 and m is preferably 0 or a whole number or a fraction greater than 0 and up to 4.

The anion X can be derived from organic or inorganic acids. Examples of organic acids are aliphatic and aromatic carboxylic acids, sulfonic acids and phosphonic acids that contain from 1 to 12, preferably from 1 to 8 and especially from 1 to 4, carbon atoms and are unsubsitituted or substituted by F or Cl. Some specific examples are formic, acetic, propionic, butyric, mono-, di- or tri-chloro- or mono-, di- or tri-fluoro-acetic acid, benzoic acid, phenylacetic acid, methyl-, phenyl- or benzyl-phosphonic acid and methyl-, phenyl-, benzyl- p-toluyl- or trifluoromethyl-sulfonic acid. Examples of inorganic acids are the hydrohalic acids, tetrafluoroboric acid, tetraphenylboric acid, hexafluorophosphoric, -arsenic, -antimonic and -bismuthic acid, and the oxy acids of the elements N, P, S, F, Cl, Br and I. Specific examples are HCl, HBr, HI, $BF_4$, $HB(phenyl)_4$, $HPF_6$, $HSbCl_6$, $HAsF_6$, $HSbF_6$, $HClO_4$, $HBrO_4$, $HIO_4$, $H_2SO_3$, $H_2SO_4$, $HNO_2$, $HNO_3$, $H_3PO_3$ and $H_3PO_4$.

Preferred acids from which $X^{n\ominus}$ in formula I can be derived are HCl, HBr, HI, $H_2SO_4$, $HClO_4$, $HClO_3$, $HBrO_4$, $HIO_4$, $HNO_3$, $H_3PO_3$, $H_3PO_4$, $CF_3SO_3H$, $C_6H_5SO_3H$, $CF_3COOH$ and $CCl_3COOH$. In a special form, $X^{n\ominus}$ in formula I is a monovalent anion (n is preferably 1), especially a halide and more especially $Cl^{\ominus}$. The iridium(III) salt of formula I is especially $IrCl_3 \cdot mH_2O$, wherein m is a number from 1 to 4.

Virtually any of the halogen compounds of the metals of the main groups and subgroups of the Periodic Table of the Elements can be used as the metal halides, provided that they are soluble in the reaction mixture and do not act as oxidising agents towards the other reactants in the reaction mixture. The use of alkali metal halides is preferred.

The metal and alkali metal cations in the metal and alkali metal halides are preferably the Li, Na, K, Rb or Cs cations, especially $Li^{\oplus}$, $Na^{\oplus}$ and $K^{\oplus}$. The ammonium cation in the ammonium halides may be $NH_4^{\oplus}$, primary ammonium having preferably from 1 to 20 carbon atoms, secondary ammonium having preferably from 2 to 24 carbon atoms, tertiary ammonium having preferably from 3 to 24 carbon atoms, and quaternary ammonium having preferably from 4 to 24 carbon atoms. Preference is given to quaternary ammonium, especially of the formula $phenylN^{\oplus}(C_1-C_6alkyl)_3$, $benzylN^{\oplus}(C_1-C_6alkyl)_3$ or $(C_1-C_6alkyl)_4N^{\oplus}$. Of the alkali metal halides and ammonium halides, the bromides and especially the iodides are preferred. In a preferred form, the alkali metal halides and ammonium halides are LiI, NaI or KI or $(C_1-C_6alkyl)_4NI$. Tetrabutylammonium iodide is especially preferred.

The diphosphines having secondary phosphine groups are preferably those (a) the phosphine groups of which are bonded to different carbon atoms of a carbon chain having from 2 to 4 carbon atoms, or (b) the phosphine groups of which are either bonded directly or via a bridge group —$CR_aR_b$ in the ortho positions of a cyclopentadienyl ring or are each bonded to a cyclo-pentadienyl ring of a ferrocenyl, or (c) one phosphine group of which is bonded to a carbon chain having 2 or 3 carbon atoms and the other phosphine group of which is bonded to an oxygen atom or a nitrogen atom bonded terminally to that carbon chain, or (d) the phosphine groups of which are bonded to the two oxygen atoms or nitrogen atoms bonded terminally to a $C_2$-carbon chain; with the result that in the cases of (a), (b), (c) and (d) a 5-, 6- or 7-membered ring is formed together with the Ir atom, and $R_a$ and $R_b$ are each independently of the other hydrogen, $C_1$–$C_8$alkyl, $C_1$–$C_4$fluoroalkyl, phenyl or benzyl or are phenyl or benzyl having from 1 to 3 $C_1$–$C_4$alkyl or $C_1$–$C_4$alkoxy substituents. Rb is preferably hydrogen. $R_a$ is preferably $C_1$–$C_4$alkyl and especially methyl.

The diphosphine contains preferably at least one chiral carbon atom and is especially an optically pure stereoisomer (enantiomer or diastereoisomer), or a pair of diastereoisomers, since the use of catalysts containing those ligands leads to optical induction in asymmetric hydrogenation reactions.

The phosphine groups contain preferably two identical or different, preferably identical, unsubstituted or substituted hydrocarbon radicals having from 1 to 20, especially from 1 to 12 carbon atoms. Preference is given to diphosphines wherein the secondary phosphine groups contain two identical or different radicals from the following group: linear or branched $C_1$–$C_{12}$alkyl; unsubstituted or $C_1$–$C_6$alkyl- or $C_1$–$C_6$alkoxy-substituted $C_5$–$C_{12}$cycloalkyl, $C_5$–$C_{12}$cycloalkyl-$CH_2$-, phenyl or benzyl; and phenyl or benzyl substituted by halogen (e.g. F, Ca or Br), $C_1$–$C_6$haloalkyl, ($C_1$–$C_{12}$alkyl)$_3$Si, ($C_6H_5$)$_3$Si, $C_1$–$C_6$haloalkoxy (e.g. trifluoromethoxy), —$NH_2$, phenyl$_2$N-, benzyl$_2$N-. morpholinyl, piperidinyl, pyrrolidinyl, ($C_1$–$C_{12}$alkyl)$_2$N—, -ammonium-$X_1^\ominus$, —$SO_3M_1$, —$CO_2M_1$, –$PO_3M_1$ or by —COO—$C_1$–$C_6$alkyl (e.g. —$COOCH_3$), wherein $M_1$ is an alkali metal or hydrogen and $X_1^\ominus$ is the anion of a monobasic acid. $M_1$ is preferably H, Li, Na or K $A_1^\ominus$, as the anion of a monobasic acid, is preferably $Cl^\ominus$, $Br^\ominus$ or the anion of a carboxylic acid, for example formate, acetate, trichloroacetate or trifluoroacetate.

A secondary phosphine group may also be a radical of the formula

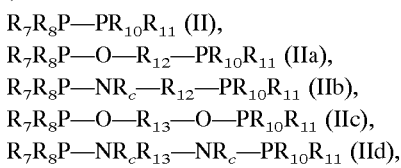, wherein m and n are each independently of the other an integer from 2 to 10, and the sum of m+n is from 4 to 12, especially from 5 to 8. Examples thereof are [3.3.1]- and [4.2.1]-phobyl of the formulae

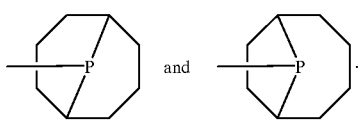

Examples of alkyl that preferably contains from 1 to 6 carbon atoms are methyl, ethyl, n-propyl, isopropyl, n-, isoand tert-butyl and the isomers of pentyl and hexyl. Examples of unsubstituted or alkyl-substituted cycloalkyl are cyclopentyl, cyclohexyl, methyl- or ethyl-cyclohexyl and dimethylcyclohexyl. Examples of alkyl-, alkoxy- or haloalkoxy-substituted phenyl and benzyl are methylphenyl, dimethylphenyl, trimethylphenyl, ethyl-phenyl, methylbenzyl, methoxyphenyl, dimethoxyphenyl, trifluoromethylphenyl, bis-tri-fluoromethylphenyl, tris-trifluoromethylphenyl, trifluoromethoxyphenyl and bis-tifluoro-methoxyphenyl. Preferred phosphine groups are those that contain identical or different, preferably identical, radicals from the group $C_1$–$C_6$alkyl; cyclopentyl and cyclohexyl that are unsubstituted or have from 1 to 3 $C_1$–$C_4$alkyl or $C_1$–$C_4$alkoxy substituents, benzyl and, especially, phenyl that is unsubstituted or has from 1 to 3 $C_1$–$C_4$alkyl, $C_1$–$C_4$alkoxy, F, Cl, $C_1$–$C_4$fluoroalkyl or $C_1$–$C_4$fluoroalkoxy substituents.

The diphosphine is preferably of formula II, IIa, IIb, IIc or IId, $R_7R_8P$—$PR_{10}R_{11}$ (II), $R_7R_8P$—O—$R_{12}$—$PR_{10}R_{11}$ (IIa), $R_7R_8P$—$NR_c$—$R_{12}$—$PR_{10}R_{11}$ (IIb), $R_7R_8P$—O—$R_{13}$—O—$PR_{10}R_{11}$ (IIc), $R_7R_8P$—$NR_cR_{13}$—$NR_c$—$PR_{10}R_{11}$ (IId), wherein $R_7$, $R_8$, $R_{10}$ and $R_{11}$ are each independently of the others a hydrocarbon radical having from 1 to 20 carbon atoms that is unsubstituted or substituted by $C_1$–$C_6$alkyl, $C_1$–$C_6$alkoxy, halogen, $C_1$–$C_6$haloalkyl, ($C_1$–$C_{12}$alkyl)$_3$Si, ($C_6H_5$)$_3$Si, $C_1$–$C_6$haloalkoxy, —$NH_2$, phenyl$_2$N—, benzyl$_2$N—, morpholinyl, piperidinyl, pyrrolidinyl, ($C_1$–$C_{12}$alkyl)$_2$N—, -ammonium-$X_1^\ominus$, —$SO_3M_1$, —$CO_2M_1$, —$PO_3M_1$ or by —COO—$C_1$–$C_6$alkyl, wherein $M_1$ is an alkali metal or hydrogen and $X_1^\ominus$ is the anion of a monobasic acid;

$R_9$ is linear $C_2$–$C_4$alkylene that is unsubstituted or substituted by $C_1$–$C_6$alkyl, $C_5$- or $C_6$-cycloalkyl, phenyl, naphthyl or by benzyl; 1,2- or 1,3-cycloalkylene or -cycloalkenylene, -bicycloalkylene or -bicycloalkenylene having from 4 to 10 carbon atoms, each of which is unsubstituted or substituted by $C_1$–$C_6$alkyl, phenyl or by benzyl; 1,2- or 1,3-cycloalkylene or -cycloalkenylene, -bicycloalkylene or -bicycloalkenylene having from 4 to 10 carbon atoms, each of which is unsubstituted or substituted by $C_1$–$C_6$alkyl, phenyl or by benzyl, and in the 1- and/or 2-positions or in the 3-position of which methylene or $C_2$–$C_4$alkylidene is bonded; 1,4-butylene substituted in the 2,3-positions by

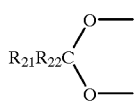

and unsubstituted or substituted in the 1,4positions by $C_1$–C6akyl, phenyl or by benzyl, wherein $R_{21}$ and $R_{22}$ are each independently of the other hydrogen, $C_1$–$C_6$alkyl, phenyl or benzyl; 3,4- or 2,4-pyrrolidinylene or 2-methylene-pyrrolidin-4-yl the nitrogen atom of which is substituted by hydrogen, $C_1$–$C_{12}$alkyl, phenyl, benzyl, $C_1$–$C_{12}$alkoxycarbonyl, $C_1$–$C_8$acyl or by $C_1$–$C_{12}$alkylaminocarbonyl; or 1,2-phenylene, 2-benzylene, 1,2-xylylene, 1,8-naphthylene, 2,2'-dinaphthylene or 2,2'-diphenylene, each of which is unsubstituted or substituted by $C_1$–$C_4$alkyl;

or $R_9$ is a radical of the formula

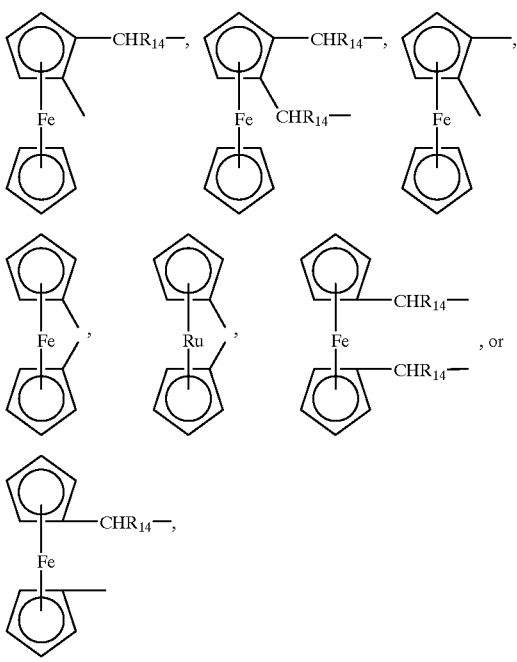

wherein $R_{14}$ is hydrogen, $C_1$–$C_8$alkyl, $C_1$–$C_4$fluoroalkyl, phenyl or phenyl having from 1 to 3 $C_1$–$C_4$alkyl or $C_1$–$C_4$alkoxy substituents;

$R_{12}$ is linear $C_2$- or $C_3$-alkylene that is unsubstituted or substituted by $C_1$–$C_6$alkyl, $C_5$- or $C_6$-cycloalkyl, phenyl, naphthyl or by benzyl; 1,2- or 1,3-cycloalkylene or -cycloalkenylene, -bicycloalkylene or -bicycloalkenylene having from 4 to 10 carbon atoms, each of which is unsubstituted or substituted by $C_1$–$C_6$alkyl, phenyl or by benzyl; or 1,2- or 1,3-cycloalkylene or -cycloalkenylene, -bicycloalkylene or -bicycloalkenylene having from 4 to 10 carbon atoms, each of which is unsubstituted or substituted by $C_1$–$C_6$alkyl, phenyl or by benzyl, and in the 1- and/or 2-positions or in the 3-position of which methylene or $C_2$–$C_4$alkylidene is bonded; 3,4- or 2,4-pyrrolidinylene or 3-methylene-pyrrolidin-4-yl the nitrogen atom of which is substituted by hydrogen, $C_1$–$C_{12}$alkyl, phenyl, benzyl, $C_1$–$C_{12}$alkoxycarbonyl, $C_1$–$C_8$acyl or by $C_1$–$C_{12}$alkylaminocarbonyl; or 1,2-phenylene, 2-benzylene, 1,2-, 2,3- or 1,8-naphthylene, each of which is unsubstituted or substituted by $C_1$–$C_4$alkyl; and $R_{13}$ is linear $C_2$alkylene that is unsubstituted or substituted by $C_1$–$C_6$alkyl, $C_5$- or $C_6$-cycloalkyl, phenyl, naphthyl or by benzyl; 1,2-cycloalkylene or -cycloalkenylene, -bicycloalkylene or -bicycloalkenylene having from 4 to 10 carbon atoms, each of which is unsubstituted or substituted by $C_1$–$C_6$alkyl, phenyl or by benzyl; 3,4-pyrrolidinylene the nitrogen atom of which is substituted by hydrogen, $C_1$–$C_{12}$akyl, phenyl, benzyl, $C_1$–$C_{12}$alkoxycarbonyl, $C_1$–$C_8$acyl or by $C_1$–$C_{12}$alkylaminocarbonyl; or 1,2-phenylene that is unsubstituted or substituted by $C_1$–$C_4$alkyl, or is a radical, less two hydroxy groups in the ortho positions, of a mono- or di-saccharide, and $R_c$ is hydrogen, $C_1$–$C_4$alkyl, phenyl or benzyl.

$R_7$, $R_8$, $R_{10}$ and $R_{11}$ are preferably identical or different, preferably identical, radicals from the following group: $C_1$–$C_6$alkyl; cyclopentyl and cyclohexyl that are unsubstituted or have from 1 to 3 $C_1$–$C_4$alkyl or $C_1$–$C_4$alkoxy substituents, benzyl and, especially, phenyl that is unsubstituted or has from 1 to 3 $C_1$–$C_4$alkyl, $C_1$–$C_4$alkoxy, F, Cl, $C_1$–$C_4$fluoroalkyl or $C_1$–$C_4$fluoroalkoxy substituents.

A preferred subgroup of diphosphines is formed by those of the formulae

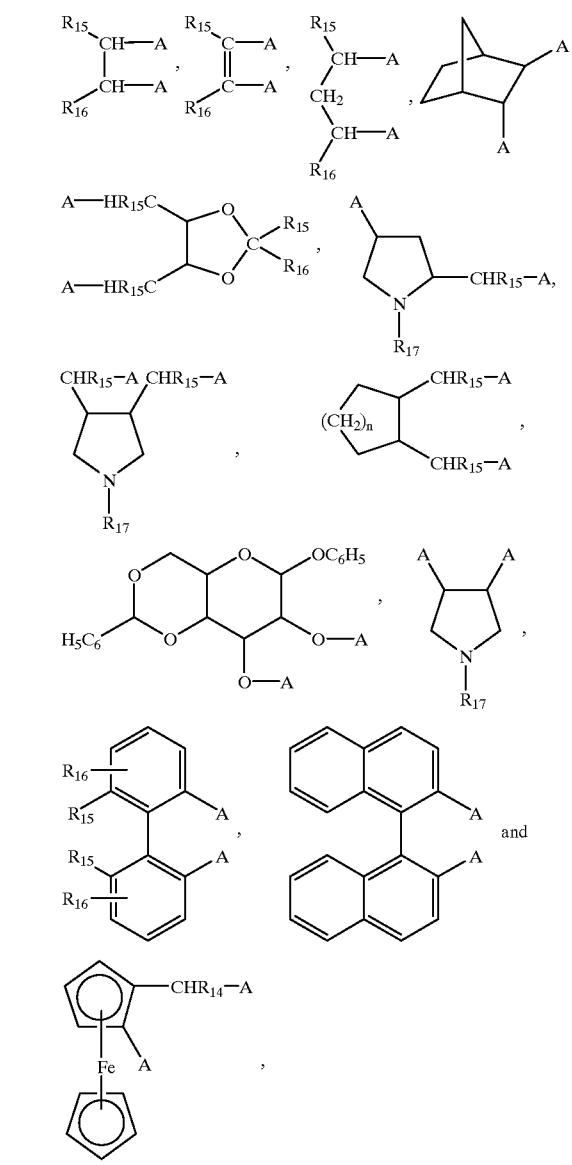

wherein $R_{15}$ and $R_{16}$ are each independently of the other hydrogen, $C_1$–$C_4$alkyl, phenyl, benzyl, or phenyl or benzyl having from 1 to 3 $C_1$–$C_4$alkyl or $C_1$–$C_4$alkoxy substituents, $R_{14}$ is hydrogen, $C_1$–$C_4$alkyl, phenyl, benzyl, or phenyl or benzyl having from 1 to 3 $C_1$–$C_4$alkyl or $C_1$–$C_4$alkoxy substituents, $R_{17}$ is hydrogen, $C_1$–$C_4$alkyl, phenyl, benzyl, $C_1$–$C_6$alkoxy—CO—, $C_1$–$C_6$alkyl—CO—, phenyl—CO—, naphthyl—CO— or $C_1$–$C_4$alkylNH—CO—, A is a diphosphine group —$PR_2$, wherein R is $C_1$–$C_6$alkyl, cyclohexyl, phenyl, benzyl, or phenyl or benzyl having from 1 to 3 $C_1$–$C_4$alkyl, $C_1$–$C_4$alkoxy, —$CF_3$ or partially or fully fluorinated $C_1$–$C_4$alkoxy substituents, and n is 0, 1 or 2.

Of those diphosphines, chirally substituted compounds are especially preferred.

Some preferred examples of diphosphines are as follows (Ph is phenyl):

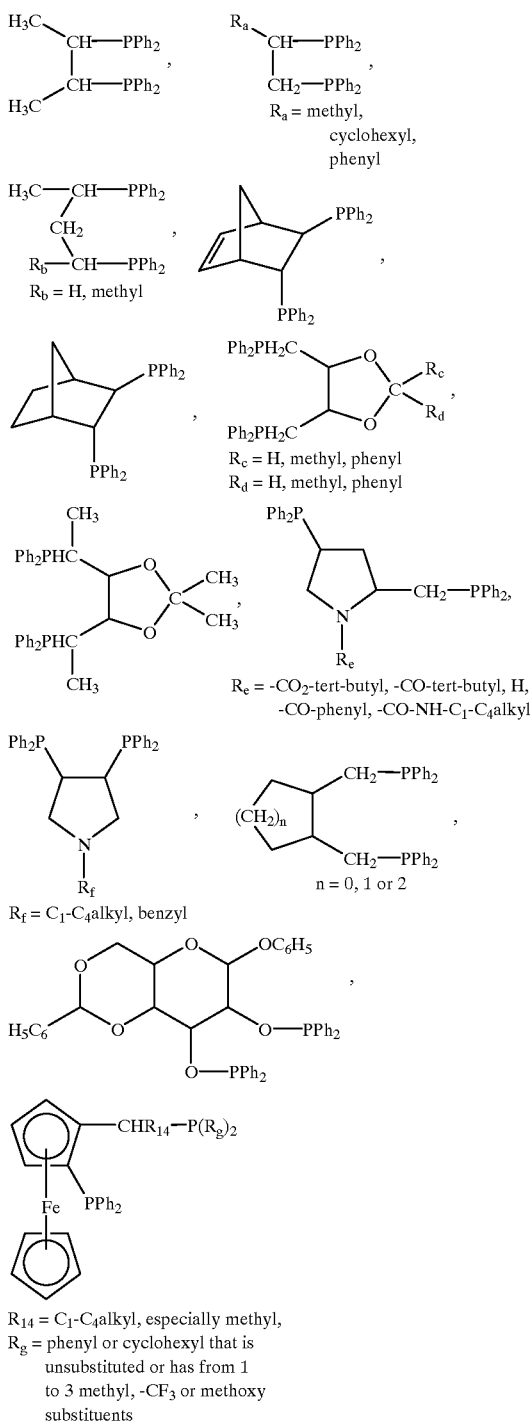

Suitable diphosphines and diphosphinites have been described, for example, by H. B. Kagan in Chiral Ligands for Asymmetric Catalysis, Asymmetric Synthesis, Volume 5, pp. 13–23, Academic Press, Inc., N.Y. (1985). The preparation of ferrocenyl diphosphine ligands is described, for example, in EP-A-0 564 406 and by T. Hayashi et al. in Bull. Chem. Soc. Jpn., 53, pages 1136–1151.

Preferred diphosphines are

{(R)-1-[(S)-2-diphenylphosphino)ferrocenyl]}ethyl-di(3,5-dimethyl-4-N,N-dipropyl-aminophenyl)phosphine {(R)-1-[(S)-2-diphenylphosphino)ferrocenyl]}ethyl-di(3,5-diisopropyl-4-N,N-dimethyl-aminophenyl)phosphine {(R)-1-[(S)-2-diphenylphosphino)ferrocenyl]}ethyl-di(3,5-diisopropyl-4-N,N-dibenzylyl-aminophenyl)phosphine {(R)-1-[(S)-2-diphenylphosphino)ferrocenyl]}ethyl-di(3,5-dimethyl-4-N,N-dibenzylyl-aminophenyl)phosphine {(R)-1-[(S)-2-diphenylphosphino)ferrocenyl]}ethyl-di(3,5-dimethyl-4-(1'-pyrrolo)-phenyl)phosphine {(R)-1-[(S)-2-diphenylphosphino)ferrocenyl]}ethyl-di(3,5-dimethyl-4-N,N-dipentyl-aminophenyl)phosphine {(R)-1-[(S)-2-diphenylphosphino)ferrocenyl]}ethyl-di(3,5-dimethyl-4N,N-dimethyl-aminophenyl)phosphine 1,4bis(diphenylphosphino)butane {(R)-1-[(S)-2di(4-methoxyphenyl)phosphino)ferrocenyl]}ethyl-di(3,5-dimethyl-4N,N-dimethylaminophenyl)phosphine and preferably {(R)-1-[(S)-2-diphenylphosphino)ferrocenyl]}ethyl-di(3,5-dimethyl-phenyl)phosphine.

The invention relates also to a process for the preparation of iridium compounds, which comprises reacting with one another at least equimolar amounts of an iridium(E) or iridium(IV) salt or a hydrate thereof and a diphosphine in the presence of an alkali metal or ammonium chloride, bromide or iodide.

The process includes the preferences indicated hereinbefore. The molar ratio of the iridium(E) or iridium(V) salt or a hydrate thereof to diphosphine may be, for example, from 1:1 to 1:1.5, preferably from 1:1 to 1:1.1. The alkali metal or ammonium chloride, bromide or iodide is preferably used in excess based on the iridium salt or the hydrate thereof. The excess may be, for example, up to fivefold, preferably up to tenfold, based on 1 mol of iridium salt or the hydrate thereof.

The process can be carried out in the absence or in the presence of a solvent. It is advantageous to use the same solvent as that to be used subsequently in the hydrogenation. Suitable solvents, which can be used alone or as a mixture of solvents, are especially dipolar solvents. Examples of solvents are: aliphatic and aromatic hydrocarbons, such as pentane, hexane, cyclohexane, methylcyclohexane, benzene, toluene and xylene; alcohols, such as methanol, ethanol, n- or iso-propanol, n-, iso- or tert-butanol, ethylene glycol, diethylene glycol, propanediols, ethylene glycol monomethyl ether or monoethyl ether, ethers, such as diethyl ether, diethylene glycol dimethyl ether, tetrahydrofuran and dioxane; halogenated hydrocarbons, such as methylene chloride, chloroform, 1,1,2,2-tetra-chloroethane and chlorobenzene; esters and lactones, such as ethyl acetate, butyrolactone and valerolactone; acid amides and lactams, such as dimethylformamide, dimethylacetamide and N-methylpyrrolidone, and ketones, such as acetone, dibutyl ketone, methyl iso-butyl ketone and methoxyacetone.

The reaction temperature may be, for example, from −20° C. to 100° C., preferably from 0° C. to 80° C. and especially from 100° C. to 70° C.

The process can be carried out, for example, as follows: the iridium salt or the hydrate thereof, a diphosphine and a metal, especially an alkali metal, or ammonium chloride, bromide or iodide, are introduced, where appropriate a solvent is added, and the mixture is stirred until the reaction is complete. The end of the reaction can be determined, for example, by chromatography by determining the consumption of phosphine or, preferably, by spectroscopy, for example by means of $^1$H-NMR. The reaction time may be, for example, up to 10, generally up to 5 and advantageously up to 2, hours. A homogeneous reaction mixture is obtained from which a solvent used concomitantly can be removed. The homogeneous residue can be isolated or used further directly as a homogeneous catalyst for hydrogenations.

The iridium compounds obtainable or prepared according to the invention are outstandingly suitable as homogeneous hydrogenation catalysts for the hydrogenation of imines, especially for the asymmetric hydrogenation of prochiral and chiral imines. Chemical conversions are frequently complete and high optical yields of over 70% or more can be achieved.

The invention relates also to a process for the catalytic hydrogenation of imines with hydrogen under elevated pressure in the presence of iridium catalysts and with or without an inert solvent, which process comprises using as catalyst an iridium compound according to the invention or an iridium compound prepared according to the invention.

In a preferred form, there is additionally added to the reaction mixture an ammonium or alkali metal chloride, bromide or iodide, especially when an excess of those halides has not been used in the preparation of the catalyst.

In a further, especially preferred form, the reaction mixture additionally contains an acid.

Suitable imines are especially those that contain at least one

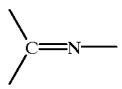

group. If the groups are substituted asymmetrically and are thus compounds having a-piochiral ketimine group, it is possible in the process according to the invention for mixtures of optical isomers or pure optical isomers to be formed if enantioselective or diastereo-selective iridium catalysts are used. The imines may contain further chiral carbon atoms. The free bonds in the above formulae may be saturated with hydrogen or organic radicals having from 1 to 22 carbon atoms or organic hetero radicals having from 1 to 20 carbon atoms and at least one hetero atom from the group O, S, N and P. The nitrogen atom of the group

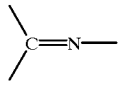

may also be saturated with $NH_2$ or a primary amino group having from 1 to 22 carbon atoms or a secondary amino group having from 2 to 40 carbon atoms. The organic radicals may be substituted, for example, by F, Cl, Br, $C_1$–$C_4$haloalkyl wherein halogen is preferably F or Cl, —CN, —$NO_2$, —$CO_2H$, —$CONH_2$, —$SO_3H$, —$PO_3H_2$, or $C_1$–$Cl_2$alkyl esters or amides, or by phenyl esters or benzyl esters of the groups —$CO_2H$, —$SO_3H$ and —$PO3H_2$. Aldimine and ketimine groups are especially reactive, with the result that using the process according to the invention it is possible selectively to hydrogenate

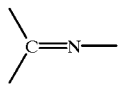

groups in addition to

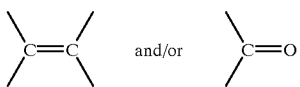

and/or groups. Aldimine and ketimine groups are also to be understood to include

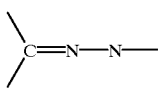

hydrazone groups.

The process according to the invention is suitable especially for the hydrogenation of aldimines, ketmines and hydrazones with the formation of corresponding amines and hydrazines, respectively. The ketimines are preferably N-substituted. It is preferable to use chiral iridium catalysts and to hydrogenate enantiomerically pure, chiral or prochiral ketimines to prepare optical isomers, the optical yields (enantiomeric excess, ee) being, for example, higher than 30%, preferably higher than 50%, and yields of more than 90% being achievable. The optical yield indicates the ratio of the two stereoisomers formed, which ratio may be, for example, greater than 2:1 and preferably greater than 4:1.

The imines are preferably imines of formula III

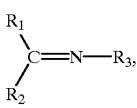

(III)

which are hydrogenated to form amines of formula IV

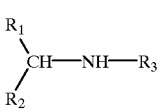

(IV)

wherein $R_3$ is preferably a substituent and wherein $R_3$ is linear or branched $C_1$–$C_{12}$alkyl, cycloalkyl having from 3 to 8 ring carbon atoms;. heterocycloalkyl bonded via a carbon atom and having from 3 to 8 ring atoms and 1 or 2 hetero atoms from the group O, S and N; a $C_7$–$C_{16}$aralkyl bonded via an alkyl carbon atom or $C_1$–$C_{12}$alkyl substituted by the mentioned cycloalkyl or heterocycloalkyl or heteroaryl;

or wherein $R_3$ is $C_6$–$C_{12}$aryl, or $C_4$–$C_{11}$ heteroaryl bonded via a ring carbon atom and having 1 or 2 hetero atoms in the ring, $R_3$ being unsubstituted or substituted by —CN, —$NO_2$, F, Cl, $C_1$–$C_{12}$alkyl, $C_1$–$C12$alkoxy, $C_1$–$Cl_2$alythio, $C_1$–$C_6$haloaulyl, —OH, $C_6$–$C_{12}$-aryl or -aryloxy or -arylthio, $C_7$–$C_{16}$-aralkyl or -aralkoxy or -aralkylthio, secondary amino having from 2 to 24 carbon atoms, —$CONR_4R_5$ or by —$COOR_4$, and the aryl radicals and the aryl groups in the aralkyl, aralkoxy and aralkylthio in turn being unsubstituted or substituted by —CN, —$NO_2$, F, Cl, $C_1$–$C_4$-alkyl, -alkoxy or -alkylthio, —OH, —$CONR_4R_5$ or by —$COOR_4$;

$R_4$ and $R_5$ are each independently of the other hydrogen, $C_1$–$C_{12}$alkyl, phenyl or benzyl, or $R_4$ and $R_5$ together are tetra- or penta-methylene or 3-oxapentylene;

$R_6$ has independently the same meaning as given for $R_4$;

$R_1$ and $R_2$ are each independently of the other a hydrogen atom, $C_1$–$C_{12}$alkyl or cycloalkyl having from 3 to 8 ring carbon atoms, each of which is unsubstituted or substituted by —OH, $C_1$–$C_{12}$alkoxy, phenoxy, benzyloxy, secondary amino having from 2 to 24 carbon atoms, —$CONR_4R_5$ or by —$COOR_4$; $C_6$–$C_{12}$aryl or $C_7$–$C_{16}$aralkyl that is unsubstituted or substituted as $R_3$, or —$CONR_4R_5$ or —$COOR_4$, wherein $R_4$ and $R_5$ are as defined hereinbefore; or $R_3$ is as defined hereinbefore and $R_1$ and $R_2$ together are alkylene having from 2 to 5 carbon atoms that is optionally interrupted by 1 or 2 —O—, —S— or —$NR_6$- radicals, and/or unsubstituted or substituted by =O or as $R_1$ and $R_2$ above in the meaning of alkyl, and/or condensed with benzene, pyridine, pyrimidine, furan, thiophene or pyrrole; or $R_2$ is as defined hereinbefore and $R_1$ and $R_3$ together are alkylene having from 2 to 5 carbon atoms that is optionally interrupted by 1 or 2 —O—, —S— or —$NR_6$- radicals, and/or unsubstituted or substituted by =O or as $R_1$ and $R_2$ above in the meaning of alkyl, and/or condensed with benzene, pyridine, pyrimidine, furan, thiophene or pyrrole.

$R_1$, $R_2$ and $R_3$ can be substituted in any desired positions by identical or different radicals, for example by from 1 to 5, preferably from 1 to 3, substituents.

The radicals $R_1$, $R_2$ and $R_3$ may contain one or more chirality centres.

Suitable substituents for $R_1$ and $R_2$ and $R_3$ are: $C_1$–$C_{12}$-, preferably $C_1$–$C_6$-, and especially $C_1$–$C_4$-alkyl, -alkoxy or -alkylthio, e.g. methyl, ethyl, propyl, n-, iso- and tert-butyl, the isomers of pentyl, hexyl, octyl, nonyl, decyl, undecyl and dodecyl, and corresponding alkoxy and alkylthio radicals;

$C_1$–$C_6$-, preferably $C_1$–$C_4$-haloalkyl having preferably F and Cl as halogen, e.g. trifluoro- or trichloro-methyl, difluorochloromethyl, fluorodichloromethyl, 1,1-difluoroeth-1-yl, 1,1-dichloroeth-1-yl, 1,1,1-trichloro- or 1,1,1-trifluoroeth-2-yl, pentachloroethyl, pentafluoroethyl, 1,1,1-trifluoro-2,2-dichloroethyl, n-perfluoropropyl, iso-perfluoropropyl, n-perfluorobutyl, fluoro- or chloro-methyl, difluoro- or dichloro-methyl, 1-fluoro- or 1-chloro-ethyl-2-yl or -ethyl-1-yl, 1-, 2- or 3-fluoro- or 1-, 2- or 3-chloro-prop-1-yl or -prop-2-yl or -prop-3-yl, 1-fluoro- or 1-chloro-but-1-yl, -but-2-yl, -but-3-yl or -but-4-yl; 2,3-dichloro-prop-1-yl, 1-chloro-2-fluoro-prop-3-yl, 2,3-dichlorobut-1-yl; $C_6$–$C_{12}$-aryl, -aryloxy or -arylthio, in which aryl is preferably naphthyl and especially phenyl, $C_7$–$C_{16}$-aralkyl, -aryloxy and -aralkylthio, in which the aryl radical is preferably naphthyl and especially phenyl and the alkylene radical is linear or branched and contains from 1 to 10, preferably from 1 to 6 and especially from 1 to 3, carbon atoms, for example benzyl, naphthylmethyl, 1- or 2-phenyl-eth-1-yl or -eth-2-yl, 1-, 2- or 3-phenyl-prop-1-yl, -prop-2-yl or -prop-3-yl, with benzyl being especially preferred; the radicals containing the aryl groups mentioned above may in turn be mono- or poly- substituted, for example by $C_1$–$C_4$-alkyl, -alkoxy or -alkylthio, halogen, —OH, —$CONR_4R_5$ or by —COORS, wherein $R_4$ and $R_5$ are as defined; examples are methyl, ethyl, n- and isopropyl, butyl, corresponding alkoxy and alkylthio radicals, F, Cl, Br, dimethyl-, methylethyl- and diethyl-carbamoyl and methoxy-, ethoxy-, phenoxy- and benzyloxy-arbonyl;

halogen, preferably F and Cl;

secondary amino having from 2 to 24, preferably from 2 to 12 and especially from 2 to 6 carbon atoms, the secondary amino preferably containing 2 alkyl groups, for example dimethyl-, methylethyl-, diethyl-, methylpropyl-, methyl-n-butyl-, di-n-propyl-, di-n-butyl-, di-n-hexyl-amino;

—$CONR_4R_5$, wherein $R_4$ and $R_5$ are each independently of the other $C_1$–$C_{12}$-, preferably $C_1$–$C_6$-, and especially $C_1$–$C_4$-alkyl, or $R4$ and $R_5$ together are tetra- or penta-methylene or 3-oxapentylene, the alkyl being linear or branched, e.g. dimethyl-, methylethyl-, diethyl-, methyl-n-propyl-, ethyl-n-propyl-, di-n-propyl-, methyl-n-butyl-, ethyl-n-butyl-, n-propyl-n-butyl- and di-n-butyl-carbamoyl;

—$COOR_4$, wherein $R_4$ is $C_1$–$C_{12}$-, preferably $C_1$–$C_6$-alkyl, which may be linear or branched, e.g. methyl, ethyl, n- and iso-propyl, n-, iso- and tert-butyl, and the isomers of pentyl, hexyl, heptyl, octyl, nonyl, decyl, undecyl and dodecyl.

$R_1$, $R_2$ and $R_3$ may contain especially functional groups, such as keto groups, —CN, —$NO_2$, carbon double bonds, N—O—, aromatic halogen groups and amide groups.

$R_1$ and $R_2$ as heteroaryl are preferably a 5- or 6-membered ring having 1 or 2 identical or different hetero atoms, especially O, S or N, which contains preferably 4 or 5 carbon atoms and can be condensed with benzene. Examples of heteroaromatics from which $R_1$ can be derived are furan, pyrrole, thiophene, pyridine, pyrimidine, indole and quinoline.

$R_1$ and $R_2$ as heteroaryl-substituted alkyl are derived preferably from a 5- or 6-membered ring having 1 or 2 identical or different hetero atoms, especially O, S or N, which contains preferably 4 or 5 carbon atoms and can be condensed with benzene. Examples of heteroaromatics are furan, pyrrole, thiophene, pyridine, pyrimidine, indole and quinoline.

$R_1$ and $R_2$ as heterocycloalkyl or as heterocycloalkyl-substituted alkyl contain preferably from 4 to 6 ring atoms and 1 or 2 identical or different hetero atoms from the group O, S and $NR_6$. It can be condensed with benzene. It may be derived, for example, from pyrrolidine, tetrahydrofluran, tetrahydrothiophene, indane, pyrazolidine, oxazolidine, piperidine, piperazine or morpholine.

$R_1$, $R_2$ and $R_3$ as alkyl are preferably unsubstituted or substituted $C_1$–$C_6$-, especially $C_1$–$C_4$-alkyl, which may be linear or branched. Examples are methyl, ethyl, iso- and n-propyl, iso-, n- and tert-butyl, the isomers of pentyl, hexyl, heptyl, octyl, nonyl, decyl, undecyl and dodecyl.

$R_1$, $R_2$ and $R_3$ as unsubstituted or substituted cycloalkyl contain preferably from 3 to 6, especially 5 or 6, ring carbon atoms. Examples are cyclopropyl, cyclobutyl, cyclopentyl, cyclohexyl, cycloheptyl and cyclooctyl.

$R_1$, $R_2$ and $R_3$ as aryl are preferably unsubstituted or substituted naphthyl and especially phenyl. $R_1$, $R_2$ and $R_3$ as aralkyl are preferably unsubstituted or substituted phenylallyl having from 1 to 10, preferably from 1 to 6 and especially from 1 to 4 carbon atoms in the alkylene, the alkylene being linear or branched. Examples are especially benzyl, and 1-phenyleth-1-yl, 2-phenyleth-1-yl, 1-phenylprop-1-yl, 1-phenylprop-2-yl, 1-phenyl-prop-3-yl, 2-phenylprop-1-yl, 2-phenylprop-2-yl and 1-phenylbut-4-yl.

In $R_2$ and $R_3$ as —$CONR_4R_5$ and —$COOR_4$, $R_4$ and $R_5$ are preferably $C_1$–$C_6$-, especially $C_1$–$C_4$-alkyl, or $R_4$ and $R_5$ together are tetramethylene, pentamethylene or 3-oxapentylene. Examples of alkyl are mentioned hereinbefore.

$R_1$ and $R_2$ together or $R_1$ and $R_3$ together as alkylene are preferably interrupted by 1 —O—, —S— or —$NR_6$-, preferably —O—. $R_1$ and $R_2$ together or $R_1$ and $R_3$ together form, with the carbon atom or with the —N=C group to which they are bonded, respectively, preferably a 5- or 6membered ring. For the substituents the preferences mentioned hereinbefore apply. As condensed alkylene, $R_1$ and $R_2$ together or $R_1$ and $R_3$ together are preferably alkylene condensed with benzene or pyridine. Examples of alkylene are: ethylene, 1,2- or 1,3-propylene, 1,2-, 1,3- or 1,4-butylene, 1,5-pentylene and 1,6-hexylene. Examples of interrupted or =O-substituted alkylene are 2-oxa-1,3-propylene, 2-oxa-1,4-butylene, 2-oxa- or 3-oxa-1,5-pentylene, 3-thia-1,5-pentylene, 2-thia-1,4butylene, 2-thia-1,3-propylene, 2-methylimino-1,3-propylene, 2-ethylimino-1,4-butylene, 2- or 3-methylimino-1,5-pentylene, 1-oxo-2-oxa-1,3-propylene, 1-oxo-2-oxa-1,4-butylene, 2-oxo-3-oxa-1,4-butylene, 1-oxa-2-oxo-1,5-pentylene. Examples of condensed alkylene are:

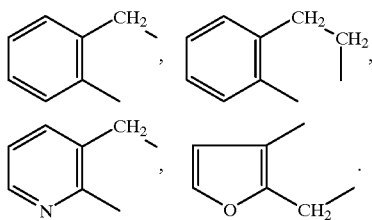

Examples of condensed and interrupted and unsubstituted or =O-substituted alkylene are:

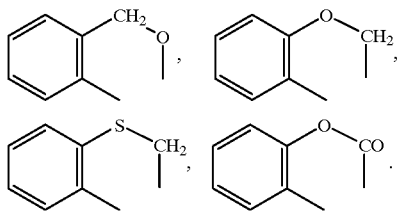

$R_4$ and $R_5$ are preferably each independently of the other hydrogen, $C_1$–$C_4$alkyl, phenyl or benzyl. $R_6$ is preferably hydrogen or $C_1$–$C_4$alkyl.

A further preferred group is formed by prochiral imines in which in formula III $R_1$, $R_2$ and $R_3$ are each different from the others and $R_3$ is not hydrogen.

In an especially preferred group, in formula III $R_3$ is 2,6di-$C_1$–$C_4$allylphen-1-yl and especially 2,6dimethylphen-1-yl or 2-methyl-6ethylphen-1-yl, $R_1$ is $C_1$–$C_4$alkyl and especially ethyl or methyl, and $R_2$ is $C_1$–$C_4$alkyl, $C_1$–$C_4$alkoxymethyl or $C_1$–$C_4$alkoxyethyl, and especially methoxymethyl.

Of those compounds, imines of formulae

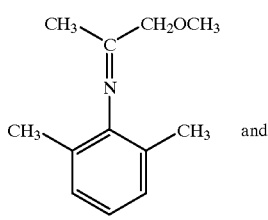

and

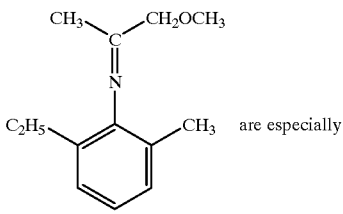

are especially important, as is the imine of the formula

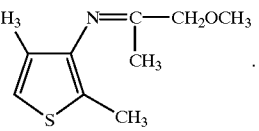

Imines of formula m are known or they can be prepared in accordance with known processes from aldehydes or ketones and primary amines.

The iridium catalysts can be added to the reaction mixture as isolated compounds. It has, however, proved advantageous to prepare the catalysts in situ with or without a solvent before the reaction and to use them further directly for the hydrogenation, for example first adding an acid to the catalyst prepared in situ.

The iridium catalysts are preferably used in amounts of from 0.0001 to 10 mol %, especially from 0.001 to 10 mol %, and more especially from 0.01 to 5 mol %, based on the imine.

The molar ratio of the imine to the iridium catalyst may be, for example, from 1 000 000 to 10, preferably from 500 000 to 20, and especially from 300 000 to 100.

The process is preferably carried out at a temperature of from −20 to 100° C., especially from 0 to 80° C. and more especially from 10 to 70° C., and preferably under a hydrogen pressure of from $2\times10^5$ to $1.5\times10^7$ Pa (from 5 to 150 bar), especially $10^6$ to $10^7$ Pa (from 10 to 100 bar).

An advantageous form of the hydrogenation process according to the invention comprises the additional use of an ammonium or alkali metal chloride, bromide or iodide. Those chlorides, bromides and iodides are preferably used in amounts of from 0.01 to 200 mol %, especially from 0.05 to 100 mol % and more especially from 0.5 to 50 mol %, based on the iridium catalyst The iodides are preferred. Ammonium is preferably tetra- alkylammonium having from 1 to 6 carbon atoms in the alkyl groups, and the alkali metal is preferably sodium, lithium or potassium. Tetrabutylammonium iodide is especially preferred.

The reaction can be carried out in the absence or in the presence of aprotic or protic solvents. Suitable solvents, which can be used alone or as a mixture of solvents, are especially aprotic solvents. Examples are:

aliphatic and aromatic hydrocarbons, such as pentane, hexane, cyclohexane, methylcyclo-hexane, benzene, toluene and xylene; ethers, such as diethyl ether, diethylene glycol dimethyl ether, tetrahydrofuran and dioxane; halogenated hydrocarbons, such as methylene chloride, chloroform, 1,1,2,2-tetrachloroethane and chlorobenzene; esters and lactones, such as ethyl acetate, butyrolactone and valerolactone; acid amides and lactams, such as dimethylformamide, dimethylacetamide and N-methylpyrrolidone, and ketones, such as acetone, dibutyl ketone, methyl isobutyl ketone and methoxyacetone. Also suitable are alkanols, such as methanol, ethanol, propanol, butanol or methoxyethanol.

A special form of the process according to the invention comprises the additional use of an acid. It may be an inorganic or, preferably, an organic acid. The acid is preferably used in at least the same molar amount as the iridium catalyst (equally catalytic amounts) and can also be used in excess. The excess may even consist in the use of the acid as solvent. Preferably from 0.1 to 50% by weight of acid is used, based on the unsaturated organic compound. In many cases it can be advantageous to use anhydrous acids.

Some examples of inorganic acids are $H_2SO_4$, highly concentrated sulfuic acid (oleum), $H_3PO_4$, orthophosphoric acid, HF, HCl, HBr, HI, $HClO_4$, $HBF_4$, $HPF_6$, $HAsF_6$, $HSbCl_6$, $HSbF_6$ and $HB(phenyl)_4$. $H_2SO_4$ is preferred.

Examples of organic acids are aliphatic or aromatic, optionally halogenated (fluorinated or chlorinated) carboxylic acids, sulfonic acids, phosphorus(V) acids (for example phosphonic acids, phosphonous acids) having preferably from 1 to 20, especially from 1 to 12 and more especially from 1 to 6, carbon atoms. Examples are formic acid, acetic acid, propionic acid, butyric acid, benzoic acid, phenylacetic acid, cyclohexanecarboxylic acid, chloro- or fluoro-acetic acid, dichloro- or difluoro-acetic acid, trichloro- or trirluoro-acetic acid, chlorobenzoic acid, methanesulfonic acid, ethanesulfonic acid, benzenesulfonic acid, chlorobenzene-sulfonic acid, trifluoromethanesulfonic acid, methylphos-phonic acid and phenylphosphonic acid. Preferred acids are acetic acid, propionic acid, trifluoroacetic acid, methanesulfonic acid and chloroacetic acid.

In detail, the process according to the invention can be carried out by first preparing the catalyst. A solution of the unsaturated organic compound is added to the catalyst solution (or vice versa) and, in an autoclave, hydrogen pressure is applied, thus removing the protective gas that is advantageously used. The reaction mixture is heated, if desired, and then hydrogenated. Where appropriate, when the reaction has ceased the reaction mixture is cooled and the autoclave is depressurised. The reaction mixture can be expelled from the autoclave under pressure with nitrogen and the hydrogenated organic compound can be isolated and purified in a manner known per se, for example by precipitation, extraction or distillation. The catalyst can then be used again, if necessary with the addition of fresh catalyst to compensate for losses.

In the case of the hydrogenation of aldimines and ketimines, the aldimines and ketimines can also be formed in situ before or during the hydrogenation. In a preferred form, an amine and an aldehyde or a ketone are mixed together and added to the catalyst solution and the aldimine or ketimine formed in situ is hydrogenated It is also possible, however, to use an amine, a ketone or an aldehyde together with the catalyst as the initial batch and to add the ketone or the aldehyde or the amine thereto, either all at once or in metered amounts. When using that method it can be advantageous to remove the water of reaction arising from the imine formation, for example by means of azeotropic distillation or by the addition of water-binding agents.

The amines that can be prepared according to the invention are biologically active compounds or are intermediates for the preparation of such compounds, especially in the field of the preparation of pharmaceuticals and agrochemicals. For example, o,o-dialkyl-arylketamine derivatives, especially those containing alkyl and/or alkoxyalkyl groups, are effective as fungicides, especially as herbicides. The derivatives may be amine salts, acid amides, for example chloroacetic acid amides, tertiary amines and ammonium salts (see, for example, EP-A-0 077 755 and EP-A-0 115 470).

The invention relates also to hydrogenation catalysts that are products of the reaction of an iridium(III) or iridium(IV) salt or the hydrates thereof with a diphosphine having secondary phosphine groups and an alki metal or ammonium chloride, bromide or iodide.

The invention relates also to the use as a hydrogenation catalyst of a reaction product of an iridium(III) or iridium (IV) salt or the hydrates thereof, a diphosphine having secondary phosphine groups and an alkali metal or ammonium chloride, bromide or iodide.

The Examples that follow illustrate the invention in more detail. The chemical conversion is determined by gas chromatography [DB 17/30 W column (15 m), manufacturer: JCW Scientific Inc. USA, temperature programme: from 60° C./1 min to 220° C., $\Delta T$: $10° \times min^{-1}$]. The optical yields (enantiomeric excess, ee) are determined either by gas chromatography [Chirasil-Val column, 50 m, manufacturer: Alltech, USA, T=150° C., isothermic], by HPLC (Chiracel OD column) or by $^1$H-NMR spectroscopy (using shift reagents).

EXAMPLE A1

Preparation of an iridium catalyst 9.1 mg (0.029 mmol) of $IrCl_3$ hydrate, 21.4 mg (0.033 mmol) of {(R)-1-[(S)-2-diphenyl-phosphino)ferrocenyl]}ethyl-di(3,5-dimethylphenyl)phosphine and 150 mg (0.4 mmol) of tetrabutylammonium iodide are dissolved in 20 ml of tetrahydrofuran and then stirred for 2 hours at 50° C. The solvent is then removed. There remains a solid soluble residue which is used further directly in Example B1.

B) Application Examples

EXAMPLE B1

Preparation of N-(2'-methyl-6'-ethyl-phen-1'-yl)-N-(1-methoxymethyl)-ethylamine

The residue from Example Al is dissolved in 2.5 ml of acetic acid. That catalyst solution and 5 ml (0.024 mol) of N-(2'-methyl-6'-ethyl-phen-1'-yl)-N-(1-methoxymethyl)eth-1-yl-ideneamine are transferred in succession to a 50 ml steel autoclave which is under an inert gas. In four cycles (10 bar, normal pressure), the inert gas is displaced by hydrogen. A pressure of 25 bar of hydrogen is then applied. After a reaction time of 10 hours at 25° C. the reaction is discontinued. The conversion is 100% and the optical yield is 78.8% (S).

EXAMPLE B2

Preparation of N-(2'-methyl-6'-ethyl-phen-1'-yl)-N-(l-methoxymethyl)ethyl-amine

A catalyst is prepared analogously to the manner described in Example A1, starting from 9.1 mg (0.029 mmol) of $IrCl_3$ hydrate, 21A. mg (0.033 mmol) of {(R)-1-[(S)-2-diphenyl-phosphino)ferrocenyl]}-ethyl-di(3,5-dimethylphenyl)phosphine and 150 mg (0.5 mmol) of tetrabutylammonium chloride in 20 ml of TBF. That catalyst is dissolved in 2.5 ml of acetic acid. The hydrogenation is then carried out analogously to Example B 1 at 60 bar of hydrogen and 25° C. The reaction time is 43 hours, the conversion 73% and the enantiomeric excess 37% (S).

EXAMPLE B3

Preparation of N-(2'-methyl-6'-ethyl-phen-1'-yl)-N-(1-methoxymethyl)ethyl-amine

The process is carried out analogously to Example B2, but with the following modified reaction conditions:

150 mg (1.3 mmol) of potassium bromide. The reaction time is 91 hours, the conversion 100% and the enantiomeric excess 63% (S).

EXAMPLE B4

Preparation of N-(2'-methyl-6'-ethyl-phen-1'-yl)-N-(1-methoxymethyl)ethyl-amine

The process is carried out analogously to Example B2, but with the following modified reaction conditions:

23.1 mg (0.033 mmol) of {(R)-1-[(S)-2-diphenylphosphino)ferrocenyl]}ethyl-di(3,5-dimethyl-4N, N-propylaminophenyl)phosphine, 150 g (0.4 mmol) of tetrabutylammonium iodide, 30 bar of hydrogen. The reaction time is 3.5 hours, the conversion 97% and the enantiomeric excess 81.7% (S).

EXAMPLE B5

Preparation of N-(2'-methyl-6'-ethyl-phen-1'-yl)-N-(1-methoxymethyl)ethylamine

The process is carried out analogously to Example B2, but with the following modified reaction conditions: 14.1 mg (0.033 mmol) of (2R,4R)-bis(diphenylphosphino)pentane, 150 mg (0.4 mmol) of tetrabutylammonium iodide, 30 bar of hydrogen. The reaction time is 21.5 hours, the conversion 95% and the enantiomeric excess 46.9% (S).

EXAMPLE B6

Preparation of N-(2'-methyl-6'-ethyl-phen-1'-yl)-N-(1-methoxymethyl)ethyl-amine

The process is carried out analogously to Example B2, but with the following modified reaction conditions:

15.4 mg (0.029 mmol) of IrBr$_3$ hydrate, 19.5 mg (0.033 mmol) of {(R)-1-[(S)-2-di-(2-methylphenyl)phosphino)fercocenyl]}ethyl-diphenylphosphine, 0.1 ml of trifluoroacetic acid in 5 ml of toluene, 150 mg (0.4 mmol) of tetrabutylammonium iodide. The reaction time is 71 hours, the conversion 15% and the enantiomeric excess 29.4% (S).

EXAMPLE B7

Preparation of N-(2'-methyl-6'-ethyl-phen-1'-yl)-N-(1-methoxymethyl)ethyl-amine

The process is carried out analogously to Example B2, but with the following modified reaction conditions:

19.9 mg (0.033 mmol) of (R)(+)-2,2'-bis(diphenylphosphino)-1,1'-binaphthalene, 0.1 ml of methanesulfonic acid in 2.5 ml of toluene and 2 ml of isopropanol, 150 mg (0.4 mmol) of tetrabutylammonium iodide, 30 bar of hydrogen. The reaction time is 56 hours, the conversion 75% and the enantiomeric excess 31%.

EXAMPLE B8

Preparation of N-(2'-methyl-6'-ethyl-phen-1'-yl)-N-(1-methoxymethyl)ethyl-amine

A catalyst is prepared analogously to the manner described in Example Al, starting from 9.1 mg (0.029 mmol) of IrCl$_3$ hydrate, 15.6 mg (0.033 mmol) of (4S,5S)-(+)4,5-bis(di-phenylphosphinomethyl)-2,2-dimethyl-1,3-dioxolane and 150 mg (0.4 mmol) of tetrabutylammonium iodide in 20 ml of THF. The catalyst is dissolved in 5 ml of isopropanol. The hydrogenation is then carried out analogously to Example B 1 at 30 bar of hydrogen and 25° C. The reaction time is 22 hours, the conversion 21%.

EXAMPLE B9

Preparation of N-(2'-methyl-6'-ethyl-phen-1'-yl)-N-(1-methoxymethyl)ethyl-amine

In succession, 5 ml (0.024 mmol) of N-(2'-methyl-6'-ethyl-phen-1'-yl)-N-(1-methoxy-methyl)ethylideneamine, 2 ml of acetic acid, 14.6 mg (0.03 mmol) of H$_2$IrCl$_6$.6H$_2$O, 21.4 mg (0.033 mmol) of {(R)-1-[(S)-2-diphenylphosphino)ferrocenyl]}ethyl-di(3,5-di-methylphenyl)phosphine and 150 mg (0.5 mmol) of tetrabutylammonium chloride are transferred to a 50 ml steel autoclave. The autoclave is then closed and placed under an argon atmosphere. Finally, the gas blanket is changed and a pressure of 25 bar of hydrogen is applied. After a reaction time of 18 hours at room temperature, a conversion of 92% and an ee of 76.6% (S) are obtained.

What is claimed is:

1. A process for the catalytic hydrogenation of an imine with hydrogen under elevated pressure in the presence of an iridium catalyst and with or without an inert solvent, in the presence of an aliphatic or aromatic carboxylic acid, sulfonic acid or phosphorus (V) acid and wherein an iridium compound obtained by the reaction of an iridium (III) or iridium (IV) salt or a hydrate thereof and a diphosphine having secondary phosphine groups in the presence of a metal or ammonium chloride, bromide or iodide is used as the catalyst.

2. A process according to claim 1, wherein the imine contains at least one

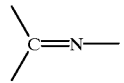

group.

3. A process according to claim 1, wherein the imine contains at groups

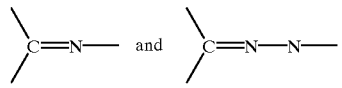

and >CN-N and additionally unsaturated groups

and

4. A process according to claim 3, wherein the free bonds are saturated with hydrogen or organic radicals having from 1 to 22 carbon atoms or organic hetero radicals having from 1 to 20 carbon atoms, and at least one hetero atom from the group O, S, N and P; or the nitrogen atom of the group

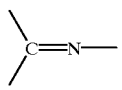

is saturated with NH₂ or a primary amino group having from 1 to 22 carbon atoms secondary amino group having from 2 to 40 carbon atoms.

5. A process according to claim 1, wherein aldimines, ketimines and hydrazones are hydrogenated.

6. A process according to claim 5, wherein the imine is an imine of formula III

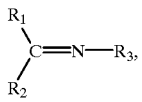 (III)

which is hydrogenated to form an amine of formula IV

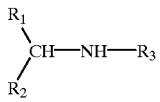 (IV)

wherein
$R_3$ is linear or branched $C_1$–$C_{12}$alkyl, cycloalkyl having from 3 to 8 ring carbon atoms; heterocycloalkyl bonded via a carbon atom and having from 3 to 8 ring atoms and 1 or 2 hetero atoms from the group O, S and $NR_6$; a $C_7$–$C_{16}$aralkyl bonded via an alkyl carbon atom, or $C_1$–$C_{12}$alkyl substituted by the mentioned cycloalkyl or heterocycloalkyl or heteroaryl;

or wherein
$R_3$ is $C_{6–C12}$aryl, or $C_4$–$C_{11}$ heteroaryl bonded via a ring carbon atom and having 1 or 2 hetero atoms in the ring; $R_3$ being unsubstituted or substituted by —CN, —NO₂, F, Cl, $C_1$–$C_{12}$alkyl, $C_1$–$C_{12}$alkoxy, $C_1$–$C_{12}$alkylthio, $C_1$–$C_6$haloalkyl, —OH, $C_6$–$C_{12}$-aryl or -aryloxy or -arylthio, $C_7$–$C_{16}$-aralkyl or -aralkoxy or -aralkylthio, secondary amino having from 2 to 24 carbon atoms, —CONR₄R₅ or by —COOR₄, and the aryl radicals and the aryl groups in the aralkyl, aralkoxy and aralkylthio in turn being unsubstituted or substituted by —CN, —NO₂, F, Cl, $C_1$–$C_4$-alkyl, -alkoxy or -alkylthio, —OH, —CONR₄R₅ or by —COOR₄;

$R_4$ and $R_5$ are each independently of the other hydrogen, $C_1$–$Cl_2$alkyl, phenyl or benzyl, or $R_4$ and $R_5$ together are tetra- or penta-methylene or 3-oxapentylene;

$R_6$ has independently the same meaning as given for $R_4$;

$R_1$ and $R_2$ are each independently of the other a hydrogen atom, $C_1$–$C_{12}$alkyl or cycloalkyl having from 3 to 8 ring carbon atoms, each of which is unsubstituted or substituted by —OH, $C_1$–$C_{12}$alkoxy, phenoxy, benzyloxy, secondary amino having from 2 to 24 carbon atoms, —CONR₄R₅ or by —COOR₄; $C_6$–$C_{12}$aryl or $C_7$–$C_{16}$aralkyl that is unsubstituted or substituted as $R_3$, or —CONR₄R₅ or —COOR₄, wherein R4 and R₅ are as defined hereinbefore; or $R_3$ is as defined hereinbefore and $R_1$ and $R_2$ together are alkylene having from 2 to 5 carbon atoms that is optionally interrupted by 1 or 2 —O—, —S— or —NR₆- radical, and/or unsubstituted or substituted by =O or as $R_1$ and $R_2$ above in the meaning of alkyl, and/or condensed with benzene, pyridine, pyrimidine, furan, thiophene or pyrrole; or $R_2$ is as defined hereinbefore and $R_1$ and $R_3$ together are alkylene having from 2 to 5 carbon atoms that is optionally interrupted by 1 or 2 —O—, —S— or —NR₆- radical, and/or unsubstituted or substituted by =O or as $R_1$ and $R_2$ above in the meaning of alkyl, and/or condensed with benzene, pyridine, pyrimidine, furan; thiophene or pyrrole.

7. A process according to claim 5, wherein $R_1$ and $R_2$ as heteroaryl form a 5- or 6-membered ring having 1 or 2 identical or different hetero atoms.

8. A process according to claim 5, wherein $R_1$ and $R_2$ as heteroaryl-substituted alkyl are derived from a 5- or 6-membered ring having 1 or 2 identical or different hetero atoms.

9. A process according to claim 5, wherein $R_1$ and $R_2$ as heterocycloalkyl or as hetero-cycloalkyl-substituted alkyl contain from 4 to 6 ring atoms and 1 or 2 identical or different hetero atoms from the group O, S and $NR_6$, wherein $R_6$ is hydrogen, $C_1$–$C_{12}$alkyl, phenyl or benzyl.

10. A process according to claim 5, wherein $R_1$, $R_2$ and $R_3$ as alkyl are unsubstituted or substituted $C_1$–$C_6$alkyl.

11. A process according to claim 5, wherein $R_1$, $R_2$ and $R_3$ as unsubstituted or substituted cycloalkyl contain from 3 to 6 ring carbon atoms.

12. A process according to claim 5, wherein $R_1$, $R_2$ and $R_3$ as aryl are unsubstituted or substituted naphthyl or phenyl, and $R_1$, $R_2$ and $R_3$ as aralkyl are unsubstituted or substituted phenylalkyl having from 1 to 10 carbon atoms in the alkylene.

13. A process according to claim 5, wherein $R_1$ and $R_2$ together or $R_1$ and $R_3$ together form, with the carbon atom or the =N=C group to which they are bonded, respectively, a 5-or 6-membered ring.

14. A process according to claim 5, wherein in formula I $R_3$ is 2,6di-$C_1$–$C_4$alkylphen-1-yl, $R_1$ is $C_1$–$C_4$alkyl, and $R_2$ is $C_1$–$C_4$alkyl, $C_1$–$C_4$alkoxymethyl or $C_1$–$C_4$alkoxyethyl.

15. A process according to claim 14, wherein $R_3$ is 2,6-dimethylphen-1-yl or 2-methyl-6-ethylphen-1-yl, $R_1$ is ethyl or methyl, and $R_2$ is methoxymethyl.

16. A process according to claim 1, wherein the acid is used in an amount of from 0.1 to 50% by weight, based on the unsaturated organic compound.

17. A process according to claim 1, wherein the organic acid is acetic acid, propionic acid, trifluoroacetic acid, chloroacetic acid or methanesulfonic acid.

18. A process according to claim 1, wherein the molar ratio of the unsaturated organic compound to the iridium catalyst is from 500 000 to 20.

19. A process according to claim 1, wherein the reaction temperature is from −20 to −100° C.

20. A process according to claim 1, wherein the hydrogen pressure is from 5 to 150 bar.

21. A process according to claim 1, wherein an aldimine or a ketimine formed in situ before or during the hydrogenation is hydrogenated.

* * * * *